United States Patent [19]

Paul et al.

[11] Patent Number: 5,683,350
[45] Date of Patent: Nov. 4, 1997

[54] ORAL TRANSLUMINATING DEVICE

[76] Inventors: Glennon H. Paul, 2420 Old Beardstown Rd.; Mark A. Heitzman, 1333 N. Rutledge St.; John P. McGee, 1825 Albert St., all of Springfield, Ill. 62702

[21] Appl. No.: 561,301

[22] Filed: Nov. 21, 1995

[51] Int. Cl.$^6$ ........................ A61B 1/06
[52] U.S. Cl. ............ 600/249; 600/241; 600/245; 362/186
[58] Field of Search ............... 600/240–241, 600/245–249; 362/171–173, 118, 186; D24/136; D26/37, 41, 50

[56] References Cited

U.S. PATENT DOCUMENTS

| | | | |
|---|---|---|---|
| 2,186,143 | 1/1940 | Neugass | 600/245 |
| 2,252,950 | 8/1941 | Seiss | 362/186 |
| 2,866,890 | 12/1958 | New | 362/186 |
| 2,885,537 | 5/1959 | Wood, Jr. | 600/248 |
| 3,349,764 | 10/1967 | Edinger et al. | 128/16 |
| 3,383,675 | 5/1968 | Allardice et al. | 362/186 |
| 3,435,820 | 4/1969 | Taur | 128/11 |
| 3,856,001 | 12/1974 | Phillips | 128/11 |
| 3,890,960 | 6/1975 | Wunsch, nee Kuhn et al. | 128/15 |
| 4,530,039 | 7/1985 | Shin-Shi | 362/186 |
| 4,643,172 | 2/1987 | Taff et al. | 128/16 |
| 4,807,599 | 2/1989 | Robinson et al. | 128/16 |
| 4,834,077 | 5/1989 | Sun | 128/11 |
| 4,996,976 | 3/1991 | Nakagawa | 128/16 |
| 5,165,781 | 11/1992 | Orak | 362/186 |

FOREIGN PATENT DOCUMENTS

| | | | |
|---|---|---|---|
| 2929-564 | 7/1979 | Germany | 600/249 |

OTHER PUBLICATIONS

Martha Ann's Gifts Catalog, Jul. 1963, p. 9 Jul. 1963.

*Primary Examiner*—Beverly M. Flanagan

[57] ABSTRACT

A portable hand-held transluminating wand is disclosed which includes a hand grip portion containing the power source and an illumination source at a narrow terminating end. The illumination source is enclosed by a slide-on transparent cover which is shaped to permit insertion into a patient's mouth and placement against the roof of the mouth without discomfort. The translucent cover is tinted red to selectively provide light of a desired bandwidth beneficial to translumination of human tissue. The cover is clear in the region to be placed in contact with the roof of the mouth so that the light emitted in this region is not diffused but remains directed toward the roof of the mouth to facilitate translumination and frosted elsewhere to inhibit light leakage from the patient's mouth when closed about the device. The wand is constructed with a multi-position switch which permits the illumination source to be turned off and on through levels of illumination.

11 Claims, 3 Drawing Sheets

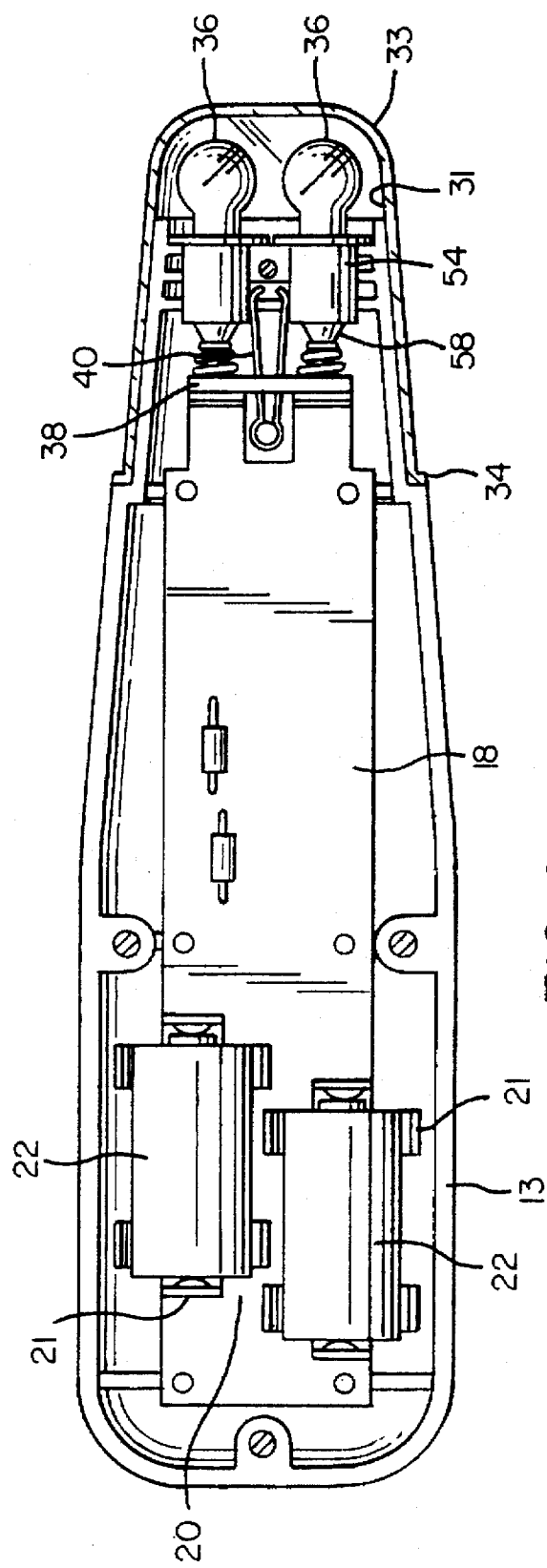
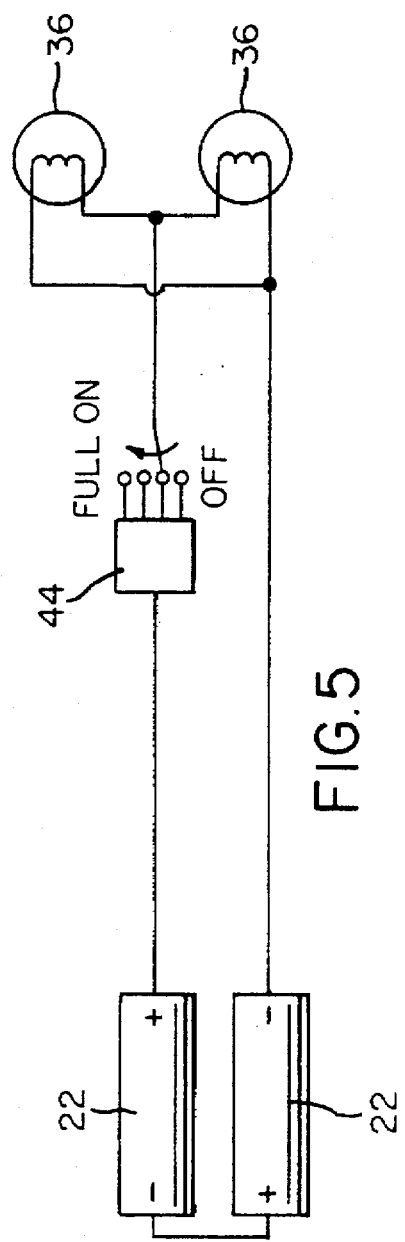
FIG. 4
FIG. 5

ORAL TRANSLUMINATING DEVICE

This invention relates to the field of medical devices, and more specifically to medical examination devices which incorporate a light.

THE PROBLEM

There are thirty-five million people in the United States who have sinus disease, and another thirty-five million people who have conditions which may seem like sinus disease such as allergic rhinitis, non-allergic rhinitis, or upper respiratory tract infections.

Currently, the diagnostic tests one would use for determining the presence or absence of sinus disease, ranked from the lowest to the highest sensitivity, would be:

a. A physical examination of the patient in search of symptoms which indicate sinus infection and responses to physician's questions provided by the patient; the sinuses themselves are not examined:

b. A sinus X-ray; or c. A modified CT scan of the sinus.

Both the latter two tests are expensive and there is a delay from the time the X-ray or CT scan is performed until the physician has the information from which a diagnosis can be made.

Although there are four known sinus cavities—the maxillary sinuses just behind the cheek bones, the frontal sinuses just above the eyes, the ethmoid sinuses which are between the nose and the eyes, and the sphenoid sinuses which are deep in the skull—it is the maxillary sinuses which are most commonly involved in sinusitis and are almost always involved even if other sinuses are involved. Therefore, if one can diagnose abnormalities in the maxillary sinus, one can be relatively sure that an individual has at least maxillary sinusitis and one can speculate, or infer that possibly other sinuses are involved.

Clearly there is a need in the art for a device which provides a better indication of the presence or absence of sinusitus, which is inexpensive to administer and which does not delay the doctor in making a diagnosis.

THE SOLUTION

The instant invention satisfies this need. The applicant has recognized that the maxillary sinuses, if backlighted with a sufficiently strong light will permit some passage of light through to the face causing the skin to "glow" or, more accurately, "transluminate" with the amount of light passage diminished by the presence of bone and fluid and tissue thickness. The applicant has also recognized that the resulting glowing pattern projected onto the skin of the face gives a useful indication of the condition of the sinuses because, while normal healthy maxillary sinus cavities will appear relatively clear and produce a translumination pattern of little variation in intensity, a maxillary sinus cavity which contains fluid or has thickened tissue associated with inflammation, infection or damage will cause the translumination to be more varied, the fluid and thicker tissue causing light passage to be reduced and the affected areas of the sinus showing as darker areas on the transluminated facial skin.

The instant invention provides a novel device to implement this diagnostic regime which can be inserted into the mouth to create the necessary backlighting and consequent translumination for diagnosis. The instant invention is a hand held, portable wand which fits easily in the hand of the physician and easily against the roof of the patient's mouth. The wand is somewhat teardrop-shaped, containing an intense light source at its narrow end powered by a self-contained power source in the thicker end of the wand which is used as a hand grip by the physician. In this context, "somewhat tear-drop shaped" means that the wand is generally rectangular at the hand grip end, with corners and edges being rounded, and the tapered end tapers away from the hand grip end, gradually reducing in thickness, to a rounded, blunt tip. As with the hand grip end, the corners and edges of the tapered end are also rounded. The wand is equipped with a thumb slide which permits the physician to control the light from the light source. The light source is covered by a tapered translucent lamp cover which is removable from the wand.

In use, the tapered end of the wand is inserted into the patient's mouth and the lamp cover is pressed gently against the roof of the patient's mouth. The patient is asked to close his mouth about the wand. The physician then darkens the room and turns on the wand light source. The resulting light is transluminated through both maxillary sinuses and against the facial tissue. As required by the individual patient's physical make-up, the physician can vary the intensity of the light by the thumb slide to adjust the light to provide the physician with what he feels is adequate backlight illumination. A reference basis is created by the physician inspecting the translumination of the skin above the cheekbone which will show the underlying bone as a darkened area compared to the transluminated skin covering the maxillary sinus cavities.

To facilitate translumination, the lamp cover is tinted red to cause the emitted light to be of a bandwidth determined most useful in the present invention. Furthermore, the lamp cover is frosted in the areas behind the light source to inhibit light from traveling back along the lamp cover then emitted about the patient's closed mouth, since such direct illumination would affect the physician's vision in the darkened examination room.

As noted, it is the maxillary sinuses which are most commonly involved in sinusitis and are almost always involved even if other sinuses are involved. In transluminating the maxillary sinuses with the wand, if there is fluid in the sinus or significant thickening of the sinus membrane, the translumination of the light will be cut down, again noting that the decreased translumination of the skin over the cheek bone provides the reference basis for any features shown in transluminating the maxillary sinuses.

The physician can, therefore, suspect that there is sinusitus in the area where there is decreased translumination of light on the face overlying the maxillary sinus cavities.

Tests have demonstrated that the wand of the instant invention can screen a patient's sinuses much more effectively than a simple physical examination. If by use of the wand, a physician can more confidently determine diagnosis, the physician can more confidently prescribe antibiotics to get complete resolution of any sinus infection. Furthermore, should the physician wish to confirm his/her clinical diagnosis of sinusitis and also check to see if there are other sinuses in the patient that are involved, indicating more extensive sinusitus, a sinus x-ray can be ordered. Advantageously, the use of the wand of the instant invention provides a diagnostic test which screens out a number of patients which might otherwise be misdiagnosed or referred on to the more accurate but expensive and time consuming X-ray or CT scan, and provides the physician with a better diagnostic basis on which to start medication even if he prefers to confirm the extent of sinusitis through either x-ray or CT scan techniques. Further, once sinusitis has been confirmed for a patient, regardless of the diagnostic method used, the instant invention provides a quick check on the progress of the patient's recovery, determined by the gradual evening and intensifying of the transluminating glow on the skin overlying the maxillary sinuses.

Although the translumination of the paranasal sinuses is admittedly not as sensitive as sinus x-rays, it is certainly much quicker and a lot less expensive and can be done right in the physicians examining room in a matter of seconds. As the physician gains experience on the use of the wand of the instant invention in diagnosing simple sinus disease, it can become a very effective adjunct in his clinical diagnostic skills.

In accordance with one aspect of the invention, a hand held portable wand is provided with a self contained power source and a source of illumination at one end;

In accordance with another aspect of the invention, a lamp cover is provided which protects the patient from heat generated by the light source and provides a comfortable surface for the wand when placed in contact with the roof of the patient's mouth.

In accordance with a further aspect of the invention, the lamp cover is translucent and tinted red to improve the quality of the light produced by the wand for translumination.

In accordance with an additional aspect of the invention, the lamp cover is frosted behind the light source to reduce the transmission of light in the direction of the wand hand grip and about the patient's mouth.

In accordance with still another aspect of the invention, the lamp cover is removable so that it can be disposed of for hygienic reasons.

In accordance with yet another aspect of the invention, the intensity of the light produced by the light source can be varied to selectively vary the translumination of the patient's skin as desired by the physician.

In accordance with a yet further aspect of the invention, the wand is so shaped and the light source control is so placed to permit the wand to fit easily in the hand of the physician; to permit the wand to fit easily in the mouth of the patient and against the roof of the patient's mouth; and to provide easy adjustment of the intensity of the light emitted from the wand with the same hand as holds the wand.

BRIEF DESCRIPTION OF THE DRAWINGS

A complete understanding of the invention will be obtained from the following disclosure taken in conjunction with the accompanying drawings in which:

FIG. 4 is a cross-section taken along line A—A in FIG. 1 showing the enclosed lamps, light sockets and batteries;

FIG. 5 is a schematic of the wiring for the lights showing the multi-position switch controlling the current to the light source and hence the intensity of illumination;

DETAILED DESCRIPTION

Figure 1:
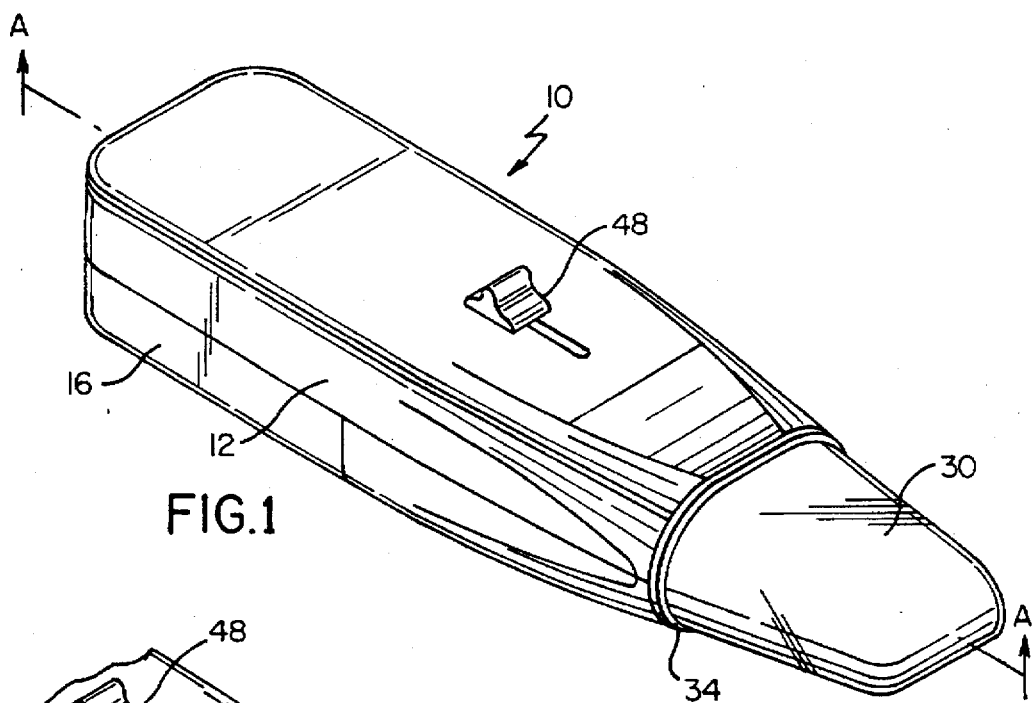
FIG. 1 is a perspective view of a preferred embodiment of the invention with the end lamp cover in position.
Figure 6:
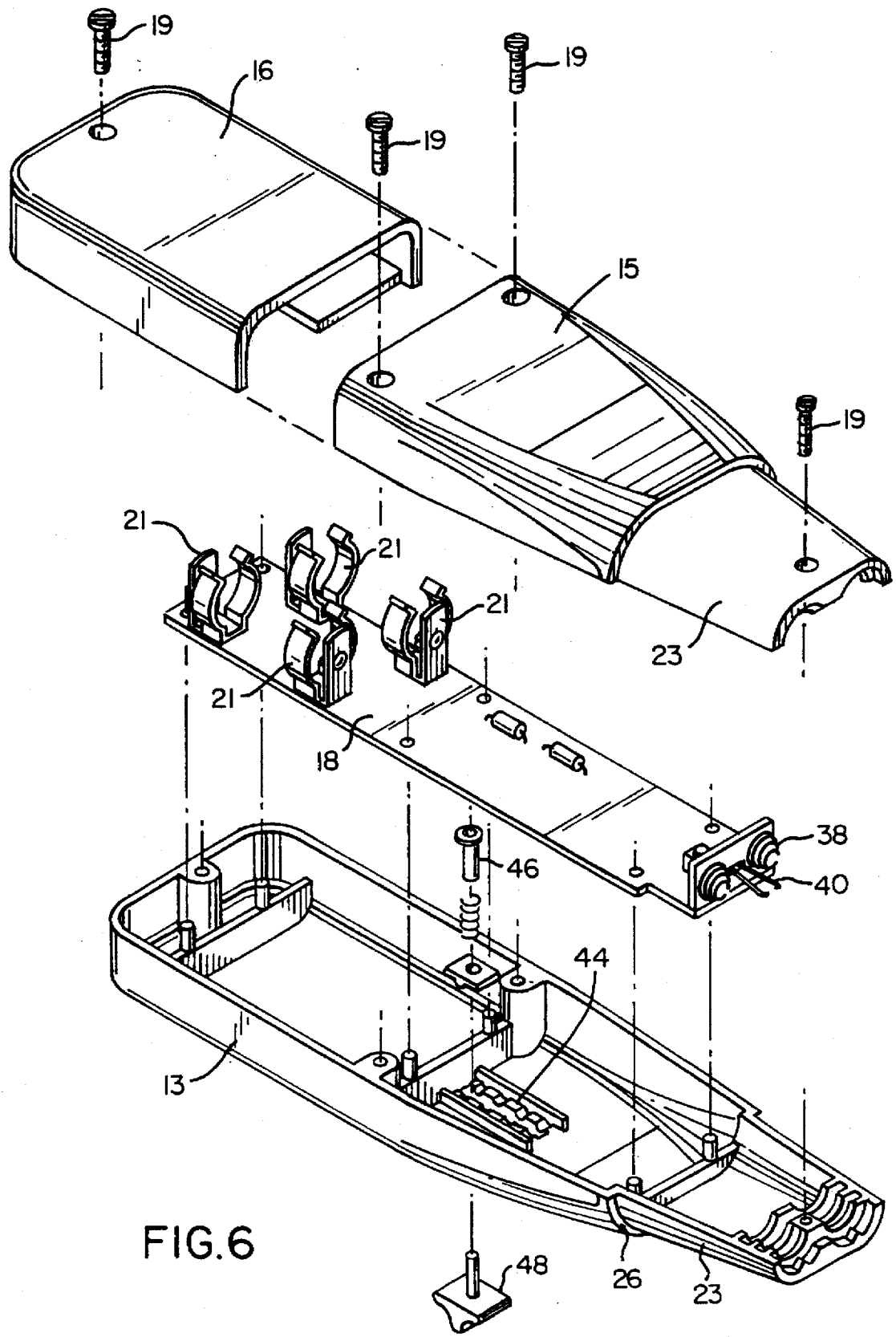
FIG. 6 is an exploded perspective of the parts making up the wand.

Referring to the drawings, and particularly FIGS. 1&6, a transluminating wand 10 constructed in accordance with the invention is illustrated and is seen to include a main body 12 and a lamp cover 30. The wand 10 is generally teardrop-shaped with the main body 12 comprising the bulbous portion of the device and the lamp cover 30 the more narrow, tapered portion. The wand 10 is ergonomicly designed such that the main body 12 fits easily into either hand of the physician, providing the physician with a ready hand grip and the lamp cover 30 fits easily into the mouth of the patient and is comfortable when pressed lightly against the roof of the patient's mouth. In describing the wand 10 as tear-drop shaped, the main body 12 and the lamp cover 30 assembled to one another as shown in FIG. 1 provide a unit which is generally rectilinear at the proximal end of the main body 12, with rounded corners and edges, and continues to be rectilinear along its length toward the distal end to which the lamp cover 30 is attached. However, some relatively small distance back from the distal end, the sides of the main body 12 commence to taper inwardly as shown in FIG. 1. Lamp cover 30 continues this general taper, primarily from the upper and lower sides as shown in FIG. 1, gradually sloping to a rounded, blunt tip having a width less than that of the main body 12.

The main body 12 is constructed in four pieces of molded plastic, such as an ABS plastic like Monsanto 633 purchased from General Polymers a division of Ashland Chemical. As shown in FIG. 6, a battery cover 16, and main body quarter panel 15 are connected to the main body upper half 13 by screws 19. Battery cover 16 incorporates a slide tongue 21 which slips beneath the abutting edge of adjacent main body quarter panel 15 and is thereby separately detachable from the main body 12 by removal of a single screw while remaining securely attached otherwise. Removal of battery cover 16 permits access to the interior of the main body 12.

Figure 2:
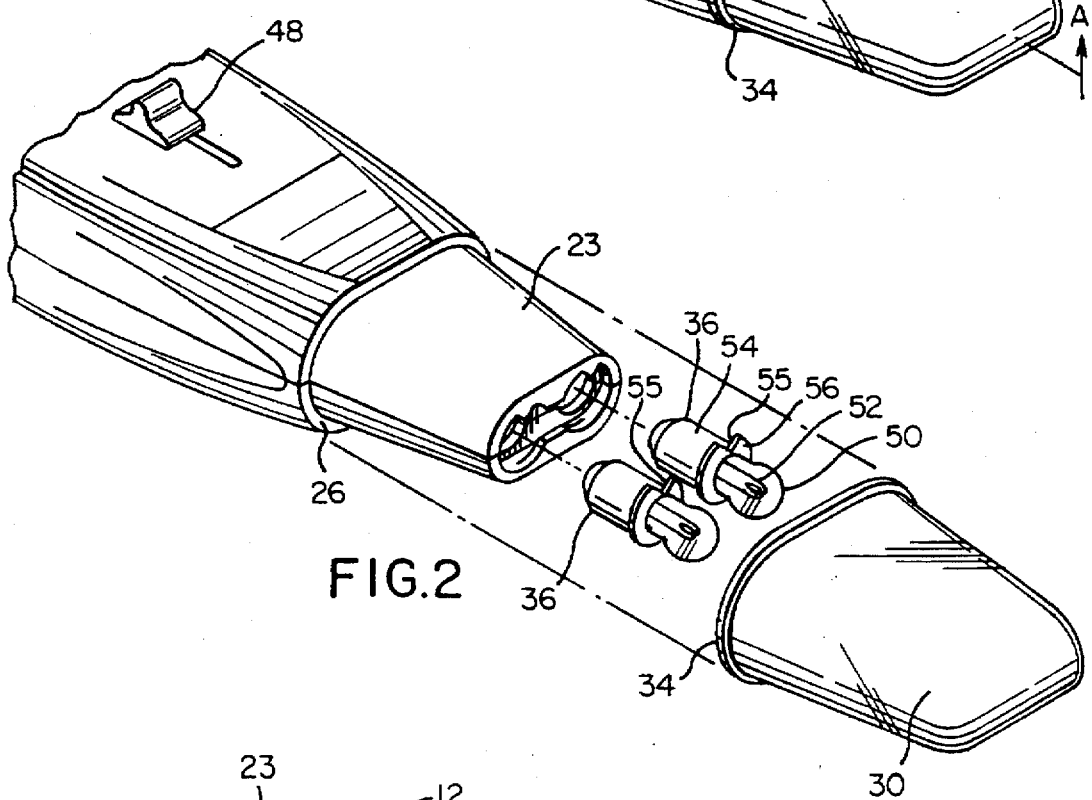
FIG. 2 is a perspective view of a preferred embodiment of the invention with the end lamp cover and light bulbs exploded from the main body of the wand.

As shown in FIG. 2, when assembled, main body 12 is tapered with a lamp cover and lamp receiving end 23 being formed inset from the otherwise gradual taper of the remainder of main body 12. This step-wise intersection of the lamp receiving end 23 with the remainder of main body 12 forms a seating ledge 26 about the circumference of the main body which provides a seating base for the lamp cover 30. The lamp receiving end 23 is shaped to conform to the inner surface of the lamp cover 30, permitting the lamp cover 30 to slide over the and about the lamp receiving end 23 and translate toward the remainder of main body 12 until ledge 26 is encountered. Further, the taper of lamp receiving end, while conforming to the inner surface of the lamp cover 30 is sized to provide a slight interference fit when the lamp cover is fully against the seating ledge 26 to assist in holding the lamp cover 30 in place.

As shown in FIGS. 4&6, within main body 12 is located a single layer circuit board 18 which contains at the hand grip end a battery connection station 20 constructed of two sets of battery clips 21 such as those available from Belford Electronics of Addison, Ill. as Keystone No. 92 battery clips. Batteries residing in the battery station 20 are preferably long life batteries such as Duracell DL2/3A, 3.0 volt Lithium/Manganese Dioxide batteries.

Figure 3:
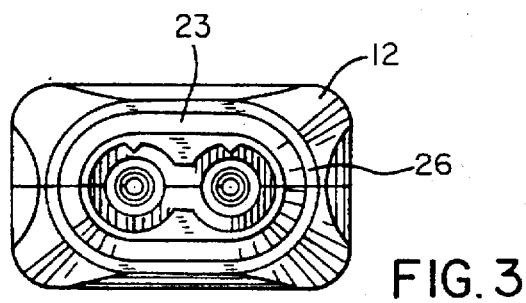
FIG. 3 is a front view of the lamp cover receiving end of the main body illustrating the insertion locations for the lamps and the locking notch to hold the lamps in place.

As shown in FIGS. 3, 4&6, the lamp cover receiving end 23 of the wand is internally shaped at its distal end to accept a light source in the form of two lamps 36 such as those manufactured by Phillips as KPR 113 4.8 volt 0.75 amp bulbs, and to act as the lamp receptacle, being notched similarly to the bulb bases to permit their insertion and rotation thereafter to a locked position. The lamps 36 are constructed of a glass bulb 50 enclosing a filament 52 which are captured at their bases in a metal base 54 which has a flared skirt 56 at the intersection between the base 54 and the bulb 50 which is notched at a single location 55. The lamp base 54 is comprised of a generally cylindrical grounding base portion 54 and a closed power tip 58 at its distal end. Also as shown in FIG. 4, a spring-loaded lamp bracket assembly 38 and a lamp ground spring clip 40 are enclosed in the lamp cover receiving end 23.

Upon insertion of the lamps 36, the bracket assembly 38 forms an electrical connection with the power tip 58 of the lamp and the clip 40 forms an electrical connection with the grounding base 54 of the lamp. Lamps 36 are powered by batteries 22, the batteries being connected in series through battery station 24. As shown in FIG. 5, the power circuit 42 between battery station 24 and lamp bracket assembly 38 incorporates a multi-position or infinite position switch 44 to enable the physician or other user of the wand of the present invention to selectively increase and decrease the power to the lamps 36, thereby increasing or decreasing their illumination. In the preferred embodiment, switch 44 is a four position spring-loaded slide switch with diodes controlling current flow, well known in the art, which can be adapted to either provide a smooth throw from OFF to FULL ON or incorporate intermediate detentes to offer specific power positions less than FULL ON. The lever 46 of the switch 44 is connected to a thumb slide 48 which is external to the main body 12 and positioned on the surface thereof in a location easily reachable and movable by the thumb of the physician's hand when holding the main body of the device during diagnostic examination.

As previously stated, the dimensions of the seating ledge 26 and the lamp cover receiving end 23 are complementary to that of inner surface 31 and lip 34 of the lamp cover 30 such that the lamp cover 30 can be inserted about lamp cover receiving end 23 and slidably translate toward the main body until lip 34 rests against seating ledge 26. There is a slight interference fit between the lamp cover inner surface 31 and the receiving end 23 to inhibit inadvertent release of the lamp cover 30 from its assembled position on the main body 12. The thickness of the lamp cover 30 and the width of the seating ledge 26 are such that there is a relatively smooth transition from the outer surface of the lamp cover 30 to the outer surface of the main body 12 adjacent the lamp cover 30, broken by the slight upset of lip 34 which provides the patient and physician a physical indication of proper insertion. The smooth and rounded contour of the lamp cover 30 provides a comfortable surface for the mouth of the patient to close about thereby further contributing to the ease of use.

Lamp cover 30 is constructed from a translucent plastic such as KRO1 K-Resin, a modified polystyrene from General Polymers which can be injection molded. Translucent meaning that light can pass easily therethrough without diffraction. The plastic is clear but tinted because the instant invention recognizes that light in the red bandwidth provides superior translumination of tissues and skin in comparision to the full bandwith of light normally provided by an incandescent bulb. In the preferred embodiment, this is transparent red dye approved by the Food and Drug Administration by regulation published in 21 CFR 178.3297 such as that available from Reed Spectrum with use permitted for all food types and conditions up through 212 degrees F. Lamp cover 30 is smooth and clear from the tip back toward lip 34 to a line about the circumference of the lamp cover at approximately the termination of lamp cover receiving end 23 when lamp cover 30 is in place on main body 12.

Commencing at that line back toward the lip 34, the lamp cover 30 is frosted both on its outside and inside surfaces 31&33, respectively, commencing at approximately the base of lamps 36 and extending downward to include the lamp cover lip 34. By tinting the lamp cover 30 red, the illumination becomes more monochromatic with red providing a good light bandwidth for translumination of tissue. Furthermore, by frosting the lamp cover 30 inner and outer surfaces 31&33, respectively, behind the lamps 36, light does not easily migrate along the lamp cover 30 behind the lamps 36 which thus reduces the light leakage from the patient's closed mouth which might otherwise affect the physician's night vision, that is, his ability to see transluminated facial areas in the darkened examination room. Conversely, by constructing the terminating end of the lamp cover 30 from the lamp bulbs position forward smooth and clear, the light emitted by the lamps 36 is not defracted. Thus the light emitted through the clear region of the lamp cover is not diffused, providing a concentrated amount of light against the area of interest, the tissue forming the roof and back of the patient's mouth.

The lamp cover 30 is tapered and rounded at its terminating end to permit comfortable insertion into the patient's mouth and placement against or near the roof of the mouth so that the maxillary sinus cavities can be properly backlighted. The lamp cover 30 provides both an insulating material and spacing between the sensitive tissue of the patient's mouth and the lamps 36 which become hot when illuminated, thus contributing to the safety of the device.

The device of the instant invention appreciates that as a consequence of being inserted into patients' mouths, measures must be taken to prevent the spread of disease from one patient to another. This is accomplished in a two-fold fashion by the instant device. First, lamp cover 30 is sized in length such that it extends a sufficient distance back from the lamps 36 that the patient's lips will close on the lamp cover 30 rather than on the main body 12 of the wand 10. In the preferred embodiment, the lamp cover 30 is approximately 2 inches in length of which 1.75 inches extends backwards from the lamps, which appears adequate for most adults. Second, the lamp cover 30 is removable and disposable so that the lamp cover 30 can be simply discarded and replaced with another rather than disinfected and reused.

In operation, the physician asks the patient to open his mouth and inserts the wand 10 so that the lamp cover 30 rests gently against the roof of the patient's mouth. The patient is then asked to close his lips about the wand 10 and the examining room is darkened. The physician then moves the thumb slide 48 toward the lamp cover 30 to power the lamps 36, increasing power and illumination by the distance the thumb slide is moved. Using the translumination of the facial skin above the cheek bone as a baseline, the physician then views the facial skin which overlays the maxillary sinuses, looking for telltale darkened areas which tend to indicate fluid build up or thickened tissue, either condition being an indication of sinusitus. Once the physician has completed his examination, the patient is asked to open his mouth and the physician removes the wand 10, subsequently detaching and disposing of the lamp cover 30.

While the device of the instant invention is described in terms of a preferred embodiment, it is recognized that suitable alternatives also may be satisfactory. For example, the lamps may be reduced or increased in number or replaced with something other than a filament type bulb. Likewise, the power source could be a rechargeable cell rather than disposable batteries. Further, the shape and size of the device can be varied to provide for easier insertion and placement, particularly when used with children rather than adults, and to conform even more closely with the physician's hand.

Consequently, it will be understood that the above description of the present invention is susceptible to various modifications, changes and adaptations, and the same are intended to be comprehended within the meaning and range of equivalents of the appended claims.

wand 10
main body 12
lamp cover 30
   inner surface 32
   lip 34
battery cover 16
inner chamber 18
battery connection station 20
batteries 22
main body lamp cover receiving end 23
seating ledge 26
lamps 36
lamp bracket assembly 38
lamp ground spring clip 40
power circuit 42
multiposition switch 44
   lever 46
   thumb slide 48

We claim:

1. A hand held portable transluminating wand to backlight the maxillary sinuses of a patient, comprising:

a generally rectilinear main body having a proximal end and a distal end, the main body tapering inwardly at the distal end and the main body sized and shaped to be a hand grip that is grasped easily in one hand;

an illumination source within the main body which emits light from the distal end of the main body;

a means in releasable engagement with the distal end of the main body for delivering light from the illumination source to the soft tissues comprising the roof of the patient's mouth, the delivery means sized and contoured to permit insertion into the patient's mouth and placement in close proximity to the roof of the patient's mouth, and also to permit closing of the patient's lips about the delivery means to prevent light from spilling from the patient's mouth, said delivery means further constructed to deliver light of only a desired bandwidth inside the patient's mouth; and a power source fully contained in the wand which provides electrical power current to the illumination source so that the illumination source can produce light and which permits the wand to be portable, whereby light from the wand can be directed against the roof of the patient's mouth while the patient's lips are closed about the delivery means to backlight the maxillary sinuses of a patient with light of a desired bandwidth permitting a physician to make an inference of the health and general state of the patient's maxillary sinuses from the light and dark areas discernable on the patient's face by the backlighting, the physician's ability to so discern enhanced by the bandwidth of the light used for the backlighting and the absence of light spilling from the patient's mouth.

2. The transluminating wand of claim 1, in which the delivery means comprises:

a translucent lamp cover, closed at one end and open at the other, which is tapered from the open end to the closed end, said open end terminating in a slightly raised lip about the circumference of the lamp cover, the lamp cover being sized and shaped to fit inside the patient's closed mouth with the raised lip remaining outside the patient's mouth;

said open end having an inner surface having complementary dimensions to the distal end of the main body from which light is emitted from the illumination source whereby the lamp cover is removably attached to the main body by insertion of the distal end of the main body into the open end of the lamp cover and the distal end of the main body and the lamp cover inner surface have a slight interference fit such that the lamp cover inner surface and the main body distal end are in pressing engagement;

the closed end of the lamp cover being relatively smooth and without sharp edges such that the closed end of the lamp cover fits comfortably against the roof of the patient's mouth; and the closed end of the lamp cover being dimensioned such that it is distanced from and surrounds the illumination source to permit light from the illumination source to enter the interior of the lamp cover from the direction of the open end and pass through the closed end of the lamp cover to thereby deliver light from the illumination source to the roof of the patient's mouth while insulating the patient's mouth from heat generated by the light source while the raised lip on the open end of the lamp cover provides an indication to the patient that the patient's lips are properly placed on the lamp cover.

3. The transluminating wand of claim 2 in which the lamp cover has two regions; a first region which is clear and which is in front of the illumination source, and a second region which is frosted, the clear region permitting light to easily pass therethrough without diffraction and the frosted region causing light to be diffracted to inhibit light transmission and leakage therethrough.

4. The transluminating wand of claim 2 in which the generally rectilinear main body of the wand is comprised of two portions, a hand grip portion which commences at the proximal end and which has rounded edges and corners and a tapered portion which likewise has rounded edges and tapers inwardly toward the distal end of the main body;

the tapered portion containing the illumination source and being circumferentially inset from the hand grip portion to form a ledge surrounding the tapered portion at the intersection with the hand grip portion; and in which the lamp cover has an inner surface and outer surface and a lip defined by the convergence of the inner surface and the outer surface, the inner surface complementing in configuration and dimension the tapered portion of the wand main body such that the lamp cover is slidably placed over the tapered portion to seat against the ledge in a slight interference fit with the tapered portion of the wand main body to thereby attach the lamp cover to the main body.

5. The transluminating wand of claim 3 in which the lamp cover is tinted red with a non-toxic, food quality dye to allow passage therethrough of light of a desired bandwidth which enhances translumination of patient's tissues.

6. The transluminating wand the claim 5 in which the second region of the lamp cover comprises all of the lamp cover behind the illumination source to thereby reduce the transmission and leakage of light in the direction of the wand main body.

7. The transluminating wand of claim 6 which is further comprised of means to selectively vary the intensity of the light produced by the illumination source.

8. A transluminating wand for backlighting the maxillary sinuses of a patient, comprising:
- a main body having a generally rectilinear main body portion shaped and dimensioned to be grasped easily in one hand with rounded edges and corners at the proximal end and continuing in such configuration toward a distal end portion which tapers inwardly while continuing to have rounded edges;
- an illumination source contained in the distal end portion;
- at the interface of the main body portion and the distal end portion, a main body ledge defined by the distal end portion being circumferentially inset from the the main body portion;
- a lamp cover, dimensioned to comfortably fit fully inside the patient's closed mouth, which tapers from an open end toward a closed end thereof and has an inner surface and an outer surface, the convergence of the inner surface and the outer surface of the lamp cover defining a lip at the open end, the lamp cover being dimensioned to translate slidably about the distal end portion of the wand main body until the lamp cover lip seats against the main body ledge, and causes a slight interference fit between the lamp cover and the main body such that the lamp cover and main body are in releasable pressing engagement, while the lamp cover closed end remains distanced from the illumination source,
- whereby, the wand is portable, the illumination source can be placed comfortably and safely inside the patient's mouth, and the lamp cover is easily removed and replaced.

9. The transluminating wand of claim 8 in which the lamp cover is tinted red and a portion thereof back from and including the closed end thereof is clear and the remainder thereof is frosted whereby transmission of light from the illumination source through the closed end is facilitated and transmission of light from the illumination source toward the open end of the lamp cover is inhibited.

10. The transluminating wand of claim 9 further comprising:
- a power source fully contained within the main body of the wand; and
- means for varying the power from the power source to the illumination source, whereby the wand is portable and able to be turned off and on through levels of illumination.

11. A transluminating wand for backlighting the maxillary sinuses of a patient by directing light against the roof of the patient's mouth, comprising:
- an illumination source;
- a disposable transparent lamp cover releasably attached to the main body, the lamp cover being the only portion of the wand which contacts the patient's lips and mouth and which directs light from the illumination source against the roof of the patient's mouth, said lamp cover tinted red such that only a desired bandwidth of light passes beyond the lamp cover against the roof of the patient's mouth and dimensioned and shaped to be comfortable when placed fully inside the patient's closed mouth; and
- means for increasing the illumination produced by the illumination source from no illumination to at least one level of illumination.

* * * * *